United States Patent [19]

Cugola et al.

[11] Patent Number: 5,374,648
[45] Date of Patent: Dec. 20, 1994

[54] INDOLE DERIVATIVES AND PHARMACEUTICAL USE THEREOF

[75] Inventors: Alfredo Cugola; Giovanni Gaviraghi; Simone Giacobbe, all of Via Alessandro Fleming, Italy

[73] Assignee: Glaxo S.p.A., Verona, Italy

[21] Appl. No.: 47,429

[22] Filed: Apr. 15, 1993

[30]    Foreign Application Priority Data

Apr. 16, 1992 [GB] United Kingdom ............... 9208492

[51] Int. Cl.$^5$ ............... C07D 209/18; C07D 405/12; A61K 31/405; A61K 31/38
[52] U.S. Cl. ............... 514/419; 548/492; 548/181; 548/235; 548/312.1; 546/273; 544/333; 514/269; 514/237.2; 514/256; 514/365; 514/375; 514/393
[58] Field of Search ........... 548/492, 181, 235, 312.1; 514/419, 269, 237.2, 256, 365, 375, 393; 544/333; 546/273

[56]       References Cited

U.S. PATENT DOCUMENTS

| | | | |
|---|---|---|---|
| 3,010,971 | 11/1961 | Kaiser et al. | 260/319 |
| 4,960,786 | 10/1990 | Salituro et al. | 514/419 |
| 5,043,334 | 8/1991 | Bell et al. | 514/207 |
| 5,145,845 | 9/1992 | Johnson et al. | 514/80 |
| 5,284,862 | 2/1994 | Bigge et al. | 514/419 |

FOREIGN PATENT DOCUMENTS

| | | |
|---|---|---|
| 0396124 | 11/1990 | European Pat. Off. . |
| WO92/01670 | 2/1992 | WIPO . |
| WO92/16205 | 10/1992 | WIPO . |

OTHER PUBLICATIONS

Salituro et al., *J. Med. Chem.*, 1992, 35, 1791–1799.
Rowley et al., *Bioorganic & Medicinal Chemistry Letters,* 1992, 2(12), 1627–1630.
Salituro et al., *J. Med. Chem.*, 1990, 33, 2946–2948.
Gray et al., *J. Med. Chem.*, 1991, 34, 1283–1292.

*Primary Examiner*—David B. Springer
*Attorney, Agent, or Firm*—Bacon & Thomas

[57]        ABSTRACT

The invention relates to compounds of formula (I).

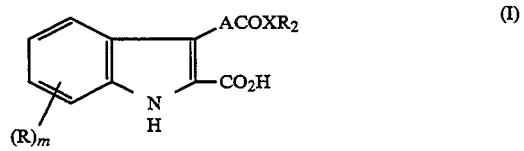

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_1$ or $COR_1$ wherein $R_1$ represents hydroxy, methoxy, or amino; m is zero or an integer 1 or 2;

A represents an ethynyl group or an optionally substituted ethenyl, or
cyclopropyl group or a substituted ethenyl group;
X represents —O— or NH;
$R_2$ represents an aryl group and when X represents an oxygen atom $R_2$ may also represent a hydrogen atom or an alkyl group; which are antagonists of excitatory amino acids, to processes for their preparation and to their use in medicine.

14 Claims, No Drawings

INDOLE DERIVATIVES AND PHARMACEUTICAL USE THEREOF

This invention relates to novel indole derivatives to processes for their preparation, to pharmaceutical compositions containing them and to their use in medicine. In particular it relates to indole derivatives which are potent and specific antagonists of excitatory amino acids.

U.S. Pat. No. 4,960,786 discloses that certain known 2-carboxylic indole derivatives are antagonists of excitatory amino acids. EP-A 0396124 also teaches that certain 2-carboxylic indole derivatives as being therapeutically effective in the treatment of CNS disorders resulting from neurotoxic damage or neurodegenerative diseases.

We have now found a novel group of 2-carboxyindole derivatives that have a highly potent and specific antagonist activity at the strychnine insensitive glycine binding site located on the NMDA receptor complex.

Accordingly the present invention provides a compound of formula (I).

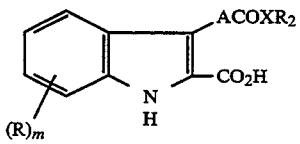

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_1$ or $COR_1$ wherein $R_1$ represents hydroxy, methoxy, or amino; m is zero or an integer 1 or 2;

A represents an ethynyl group, an optionally substituted cyclopropyl group or a substituted ethenyl group;

X represents —O— or NH;

$R_2$ represents an aryl group and when X represents an oxygen atom $R_2$ may also represent a hydrogen atom or an alkyl group;

The compounds represented by formula (I) can exist in more than one isomeric form. Thus when the group A in compounds of formula (I) is a substituted ethenyl or optionally substituted cyclopropyl group there can exist cis and trans isomers and the invention includes all such isomers and mixtures thereof.

For use in medicine the salts of the compounds of formula (I) will be physiologically acceptable thereof. Other salts however may be useful in the preparation of the compounds of formula (I) or physiologically acceptable salts thereof. Therefore unless otherwise stated references to salts includes both physiologically acceptable salts and non-physiologically acceptable salts of compounds of formula (I).

Suitable physiologically acceptable salts of compounds of the invention include base addition salts and where appropriate acid addition salts.

Suitable physiologically acceptable base addition salts of compounds of formula (I) include alkali metal or alkaline metal salts such as sodium, potassium, calcium, and magnesium, and ammonium salts formed with amino acids (e.g. lysine and arginine) and organic bases ( e.g. procaine, phenylbenzylamine, ethanolamine diethanolamine and N-methyl glucosamine).

It will be appreciated that the compound of formula (I) may be produced in vivo by metabolism of a suitable prodrug. Such prodrugs may be for example physiologically acceptable metabolically labile esters of compounds of the general formula (I). These may be formed by esterification, for example of any of the carboxylic acid groups in the parent compound of general formula (I) with where appropriate prior protection of any other reactive groups present in the molecule followed by deprotection if required. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters) or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-methoxy-1-methyl-ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1 -cyclohexyloxycarbonyloxyethyl, 1 -(4-tetrahydropyranyloxycarbonyloxyethyl) or 1-(4-tetrahydropyranylcarbonyloxyethyl.

Preferred metabolically labile esters of compounds of formula (! ) include $C_{1-4}$alkyl esters more particular methyl or ethyl, aminoalkyl esters more particular 2-(4'-morpholino)ethyl, or acyloxyalkyl esters e.g. acetoxymethyl, pivaloxymethyl, 1-cyclohexyloxycarbonyloxyethyl or 1-(4-tetrahydropyranyloxycarbonyloxy)ethyl.

The compounds of formula (I) and salts and metabolically labile esters thereof may from solvates e.g. hydrates and the invention includes such solvates.

In the compounds of formula (I) the group R may be at any of the four possible positions on the fused benzene ring and when m is 2 the two R groups may be the same or different.

The term alkyl as used herein as a group or part of a group refers to a straight or branched chain alkyl group containing from 1 to 4 carbon atom examples of such groups include methyl, ethyl propyl, isopropyl, n-butyl, isobutyl, secondary butyl or tertiary butyl.

The term halogen refers to a fluorine, chlorine or bromine atom.

The term substituted ethenyl means an ethenyl group substituted by 1 or 2 alkyl groups e.g. methyl groups and includes both the cis and trans conformations. Examples of such groups include 1-methylethenyl, 2-methylethenyl and/or 1,2-dimethylethenyl.

The term optionally substituted cyclopropyl means a cyclopropyl group optionally substituted by 1, 2 or 3 alkyl groups e.g. methyl groups.

For the group $R_2$ the term aryl means an optionally substituted phenyi group, or a 5 or 6 membered heteroaryl group, in which the 5-membered heteroaryl group contains 1 or 2 heteroatoms selected from oxygen, sulphur or nitrogen and the 6 membered heteroaryl group contains 1 or 2 nitrogen atoms. Examples of suitable heteroaryl groups include furanyl, thienyl, imidazolyl, thiazolyl, oxazolyl, pyridinyl and pyrimidinyl.

The term substituted phenyl refers to a phenyl group substituted with up 3 substituents selected from halogen, $C_{1-4}$alkyl, $C_{1-4}$alkoxy, amino, alkylamino, dialkylamino, trifiuoromethyl, trifluoromethoxy, hydroxy, cyano, nitro, amino, $SO_2R_1$ or $COR_1$ when there is more than one substitutent present these may be the same or different.

A preferred class of compounds of formula (I) are those wherein R is chlorine, m is 1 or 2 and R is at the 4 and/or 6 position, and more particularly m is 2.

When A is a substituted ethenyl group it is preferably in the E conformation.

When the group $R_2$ is a substituted phenyl group the phenyl moiety is preferably substituted by one or more groups selected from alkoxy, alkyl. amino, alkylamine, dialkylamino, fiuoro, chloro, hydroxy, nitro, trifluoromethyl or $COR_1$, wherein $R_1$ is hydroxy or methoxy.

A preferred class of compound of formula (I) are those wherein $R_2$ is phenyl or phenyl substituted by one or two groups selected from fluorine trifluoromethyl, alkyl e.g. methyl or isopropyl, hydroxy, alkoxy e.g. methoxy or ethoxy or nitro or more especially $R_2$ is phenyl.

A further preferred class of compounds of formula (I) are those wherein X is NH.

A preferred group of compounds of formula (I) are those wherein R is chlorine and m is 1 or more preferably 2, X is NH or O and $R_2$ is an optionally substituted phenyl group. From within this group particularly preferred compounds include those wherein X is NH.

A further preferred group of compounds of formula (I) are those wherein A represents an ethynyl group or a substituted ethenyl group such as 1-methlyethenyl. From within this group particularly preferred compounds includes those wherein X is NH and $R_2$ is optionally substituted phenyl, and more especially phenyl.

Particularly preferred compounds of the invention include 3-[2-(phenylcarbamoyl)ethynyl]-4,6-clichloroindole-2 -carboxylic acid, physiologically acceptable salts and metabolically labile esters thereof; and 3-[2-(phenylcarbamoyl) propenyl]-4,6-dichloroindole-2-carboxylic acid, physiologically acceptable salts and metabolically labile esters thereof;

The compounds of formula (I) and or physiologically acceptable salts thereof are excitatory amino acid antagonists. More particularly they are potent antagonists at the strychnine insensitive glycine binding site associated with the NMDA receptor complex. As such they are potent antagonists of the NMDA receptor complex. Moreover the compounds of the invention exhibit an advantageous profile of activity including good bioavailibility. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are useful in the treatment of chronic neurodegenerative diseases such as; Huntingdon's disease, Alzheimer's senile dementia, amyotrophic lateral sclerosis, Glutaric Acidaemia type, multi-infarct dementia, status epilecticus, contusive injuries (e.g. spinal cord injury), viral infection induced neurodengeration, (e.g. AIDS, encephalopaties), Down syndrome, epilepsy, schizophrenia, depression, anxiety, pain, neurogenic bladder, irritative bladder disturbances, drug dependency, including withdrawal symptoms from alcohol, cocaine, opiates, nicotine, benzodiazepine.

The potent and selective action of the compound of the invention at the strychnine-insensitive glycine binding site present on the NMDA receptor complex may be readily determined using conventional test procedures. Thus the ability to bind at the strychnine insensitive glycine binding site was determined using the procedure of Kishimoto H. et al. J Neurochem 1981, 37 1015-1024. The selectivity of the action of compounds of the invention for the strychnine insensitive glycine site was confirmed in studies at other ionotropic known excitatory amino acid receptors. Thus compound of the invention were found to show little or no affinity for the kainic acid (kainate) receptor, a-amino-3-hydroxy-5-methyl-4-isoxazole-proprionic acid (AMPA) receptor or at the NMDA binding site.

Compounds of the invention have also been found to inhibit NMDA induced convulsions in mice using the procedure Chiamulera C. et al. Psychopharmacology (1990) 102, 551-552.

The invention therefore provides for the use of a compound of formula (I) and or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically iabile ester thereof for the manufacture of a medicament for antagonising the effects of excitatory amino acids upon the NMDA receptor complex.

According to a further aspect the invention also provides for a method for antagonising the effects of excitatory amino acids upon the NMDA receptor complex, comprising administering to a patient in need thereof an antagonistic amount of a compound of formula (I) and/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 20-100mg preferably 60-80 mg per day. For oral administration a daily dose will typically be within the range 200-800 mg e.g. 400-600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt or metabilcially lablie ester thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, or rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multidose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, tirchlorofluoromethane, dichloro-tetrafluoroethane, carbon dioxide or other suitable propellant, such as dichlorodifluoromethane, trichlorofluoromethane, dichloro-tetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in for example capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramusculady) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups R, $R_1$ and $R_2$ are as defined for the compounds of formula (I) unless otherwise stated.

Compounds of formula (I) wherein A is substituted ethenyl group may be prepared from compound (II) in which R, m and n have the means given above, $R_3$ is a carboxyl protecting group, and $R_4$ is a hydrogen atom or a $C_{1-4}$alkyl group.

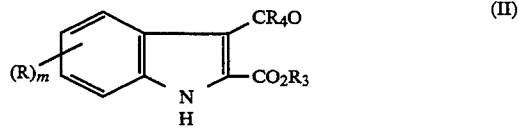

by reaction with an appropriate phosphorus ylide capable of convening the group $CR_4O$ into the group $ACOXR_2$ wherein X and $R_2$ have the meanings defined above for formula (I) followed where necessary or desired by removal of the carboxyl protecting group.

Suitable carboxyl protecting groups include allyl, alkyl, trichloroalkyi, trialkylsilylalkyl or arymethyl groups such as benzyl, nitrobenzyi or trityl. In one embodiment of this process the reaction may be carried using a phosphorus ylide of formula (III)

wherein $R_5$ is an alkyl or phenyl group, and X and $R_3$ have the meanings defined above.

The reaction is carried out in aprotic solvent such as acetonitrile or an ether such as 1,4-dioxane and preferably with heating e.g. 40°–120°. In a further embodiment of the process the reaction is carried out using a phosphorus ylide of formula (IV)

wherein $R_6$ represents hydrogen or $C_{1-4}$alkyl. $R_7$ represents $C_{1-4}$alkyl and X and $R_2$ have the meanings defined.

The reaction is carried out in an aprotic solvent such as tetrahydrofuran and optionally with heating.

Compounds of formula (I) wherein A is an optionally substituted cyclopropyl group may be prepared by treating the olefin (V)

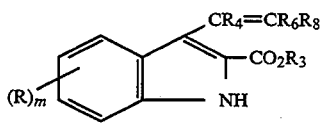 (V)

$N_2=CHCOXR_2$ (VI)

wherein R, $R_3$, $R_4$, $R_6$, and m have the meanings defined above and $R_8$ is a hydrogen atom or a $C_{1-4}$alkyl group, with the diazo derivative (VI), wherein the groups X and $R_2$ are as defined above, followed where necessary or desirable by removal of the carboxyl protecting group $R_3$. The reaction is carried out in a solvent such as 1,2-dimethoxyethane and in the presence of a Rhodium (11) catalyst such as rhodium acetate or pivalate.

Compounds of formula (I) wherein A is an ethynyl group may be prepared by reaction of the alkyne of formula (VII)

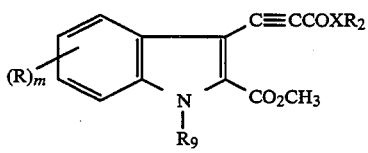 (VII)

wherein R, m X and $R_2$ have the meanings defined in formula (I) and $R_9$ represents the group $(CH_3)_3SiCH_2CH_2OCH_2-$, with hydrochloric acid in ethanol, followed by reaction with a suitable base such as lithum hydroxide.

Compounds of formula (I) wherein A is an optionally substituted cyclopropyl group may be prepared by reaction a compound of formula (I) wherein A is an optionally substituted ethenyl group, or a protected derivative thereof, e.g. an ester thereof with diazomethane in the presence of palladium acetate, followed where necessary or desired by the removal of any protecting group. The reaction is carried out in an aprotic solvent e.g. dichloromethane and/or an ether and preferably at a temperature within the range 0°-20°.

In any of the above reactions the carboxyl protecting group $R_3$ may be removed by conventional procedures known for removing such groups. Thus the group $R_3$, may be removed by hydrolysis using an alkali metal hydroxide e.g. lithium hydroxide in a solvent such as ethanol, followed where desired or necessary by that addition of a suitable acid e.g. hydrochloric acid to give the corresponding free carboxylic acid.

Physiologically acceptable salts of compounds of formula (I) may be prepared by treating the acid with the appropriate base e.g. alkali or alkaline earth metal hydroxide in an appropriate solvent such as an alkanol e.g. methanol.

Metabolically lablie esters of compounds of formula (I) may be prepared by esterification of the carboxylic acid group or a salt thereof or by trans esterfication using conventional procedures. Thus for example acyloxyalkyl esters may be prepared by reacting the free carboxylic acid or a salt thereof with the appropriate acyloxylalkyl halide in a suitable solvent such as dimethylformamide. For the esterifcation of the free carboxyl group this reaction is preferably carried out in the presence of a quaternary ammonium halide such as tetrabutylammonium chloride or benzyltriethylammonium chloride.

Aminoalkyl esters may be prepared by transesterfication of a corresponding alkyl ester e.g. methyl or ethyl ester by reaction with the corresponding aminoalkanol at an elevated temperature e.g. 50°-150°.

Compounds of formula (II) wherein $R_3$ is a carboxyl protecting group, $R_4$ is hydrogen may be prepared by treating the corresponding indole (VIII).

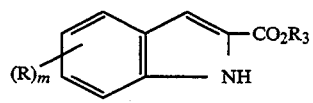 (VIII)

wherein R and m are as defined in formula (I) with N-methylformanilide and phosphorous oxychloride in a solvent such as 1,2-dichloroethane. Compounds of formula (II) wherein $R_3$ is a carboxyl protecting group, $R_4$ is alkyl and n is zero may be prepared by treating the indole (VIII) with the amide $(CH_3)_2NCOR_4$ and phosphorous oxychloride in a suitable solvent.

Compounds of formula (V) may be prepared by treating the corresponding compound of formula (II) with a reagent capable of introducing the group $CR_4=CR_6R_8$.

Thus reaction of a compound of formula (II) witn the triphenylphospine derivative $Ph_3P+CH_2R_6Br^-$ in the presence of a suitable base such as butyl lithium and in an aprotic solvent will give the corresponding compound of formula (V) wherein $R_8$ is hydrogen.

Compounds of formula (V) wherein $R_4$ represents hydrogen and $R_6$ and $R_8$ independently represent $C_{1-4}$alkyl may be prepared by treating a compound of formula (II) in which $R_4$ represents hydrogen with the disubstituted ylide $R_6R_8-C-P+Ph_3$ in a suitable solvent such as N,N-dimethylformamide. Preferably the disubstituted ylide is prepared in situ by treating the trimethylsilyl derivative $(CH_3)_3SiCR_6R_8P+Ph_3$ $Y^-$ wherein Y is an anion, with cesium fluoride. The trimethylsilyl derivative may be prepared by the method of Bestmann and Bomhard. Angew Chem. Int. Ed. Eng. 21 (1982) NO. 7 pages 545-546.

Compounds of formula (V) wherein $R_4$, $R_6$ and $R_8$ are each an alkyl group may be prepared from the corresponding compound of formula (II) by reaction with the phenylsulphonate $(PhSO_2CHR_6R_8)$. The reaction may be carried out using the general reaction procedure described by Julia and Paris. Tetrahedron Letters No. 49, 4833-4836 1973.

The compounds of formula (VII) may be prepared by reaction of the bromo acid (IX)

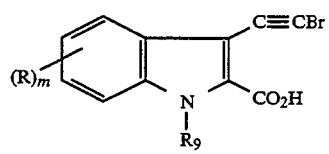 (IX)

with the appriate isocyanate $R_2NCO$ or chloroformate $R_2OCOCl$ in the presence of a suitable base such as t-butyl lithium and, in an aprotic solvent such as tetrahydrofuran and subsequent reaction of the crude reaction product with trimethylsilyldiazemethane $(CH_3)_3SiCHN_2)$. The bromo (IX) acid may be prepared from the indole (II) wherein $R_4$ is hydrogen by the following reaction sequence.

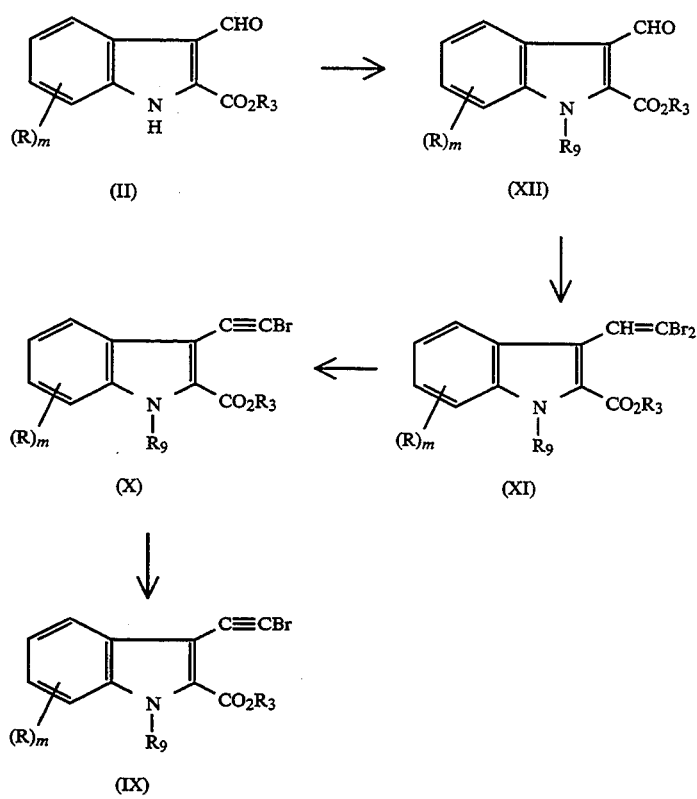

The compounds of formula (IX) may be prepared by alkaline hydrolysis of the corresponding ester (X). The ester (X) may be prepared from the corresponding dibromothene (XI) by reaction with a suitable base such as lithium bis-trimethylsilylamide in a solvent such as an ether e.g. tetrahydrofuran. The dibromoethene (XI) may be prepared from the corresponding aldehyde (XII) by reaction with triphenylphospine and carbon tetrabromide in a solvent such as dichloromethane. The N-protected indole (XII) may be prepared from the indole (II; $R_4$=H) by reaction with trimethylsilylethoxymethylchloride in the presence of a base such as sodium bis-trimethylsilylamide in a polar aprotic solvent such as dimethylformamide.

The indoles of formula (VIII) are either known compounds or may be prepared by analogus methods to these described for the known compounds.

In order that the invention may be more fully understood the following examples are given by way of illustration only.

In the Intermediates and Examples unless otherwise stated: Melting points (m.p.) were determined on a Gallenkamp m.p. apparatus and are uncorrected. All temperature refer to C.Infrared spectra were mesured on a FT-IR instrument. Proton Magnetic Resonance ($^1$H-NMR) spetra were recorded at 300 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Colum chromathography was carrier out over silica gel (Merck AG Darmstaadt, Germany). The following abbreviations are used in text: EA=ethyl acetate, CH=cyclohexane, DCM=dichlormethane, DBU=1,8 diazabicyclo [5.4.0]undec-7-ene. DMF=NM -dimethylformamide, T H F=tetrahydrofuran, LiOH.H$_2$O lithium hydroxide monohydrate. Tlc refers to a thin layer chromatography on silica plates. Solution were dried over anhydrous sodium sulphate.

Intermediate I

Ethyl. 4,6-dichloroindole-2-carboxylate

To a solution of ethyl pyruvate (2.05 ml), in absolute ethanol (38 ml), concentrated sulphuric acid (0.5 ml) was added slowly under vigorous stirring.

The resulting mixture was stirred at 23 for 10 minutes, then 3,5-dichlorophenylhydrazine hydrochloride (4 g) was added portionwise. The mixture was heated to reflux for 4 hours, cooled to 23°, poured into cold water (500 ml) and extracted with diethyl ether (3×300 ml). The organic layers were separated and dried. The solvent was evaporated under reduced pressure to give the 2-(3,5-dichlorophenylhydrazone)propionic acid ethyl ester as yellow solid (5 g; tlc DCM, Rf=0.79, 0.47) in E and Z isomers mixture. The solid was added to polyphosphoric acid (20 g) under stirring and the mixture was heated at 45° for 20 minutes to give a brown product which was crystallized by 95% ethanol (300 ml) to obtain the title compound as a yellow-brown solid (3.3 g;m.p.180°; Tlc DCM, Rf=0.54). IR(CDCl$_3$) Vmax(cm$^{-1}$)3440(NH), 1772-1709(C=O).

Intermediate 2

Ethyl 3-formyl-4,6-dichloroindole-2-carboxylate

A solution of N-methyl formanilide (5.19 g) and phosporous oxychloride (5.53 g) was stirred at 23° for 15 minutes. 1,2-Dichloroethane (60 ml) and intermediate I (6 g) were added and the resulting suspension was stirred at 80° for 6 hours. The reaction mixture was poured into a 50% aqueous solution of sodium acetate (300 ml) to give, by filtration, the title compound as a yellow solid (4.1 g; tlc EA/CH:4/6, Rf=0.4).

Intermediate 3

Ethyl 3-formyl- 1 -(2-trimethylsilyl-ethoxymethyl)-4,6-dichloroindole-2-carboxylate acid To a cooled solution of intermediate (2) (700 mg) in dry DMF (20 ml) at 0° was added lithium bis-trimethylsilylamide (3.7 ml), 1M solution) in THF. The mixture was stirred for 15 minutes at 0°, then tri-methylsilylethoxymethyl chloride (0.817 g) was added. After one hour the resulting mixture was poured into water (25 ml) and extracted with ethyl acetate (3×20 ml). The combined organic layers were dried and concentrated under vacuum. The residue was purified by chromatography on silica gel to afford the title compound (950 mg) as a pale yellow solid. Rf=0.3EA/CH: 1.9.

Intermediate 4

Ethyl 3-(2,2-dibromovinyl)-1-(trimethylsilyl-ethoxymethyl) -4.6-dichloroindole-2-carboxylate Intermediate 3 (300 mg) was dissolved in dry dichloromethane (7 ml) and the solution was cooled to −15° with an ice/salt bath. Then, triphenylphosphine (1.14 g) and carbon tetrabromide (719 ml) were added and the resulting solution was stirred for 1.5 hrs, while the temperature was gradually increased to 0°. Saturated NH$_4$Cl (20 ml) was then added, the two phases separated and the water phase extracted twice with dichloromethane. The combined organic phase was dried, concentrated and the obtained residue was passed through a silica gel pad (CH/EA:9/1) to give the title compound (390 mg) as a yellow oil. Rf=0.62 CH/EA: 9/1

Intermediate 5

Ethyl 3-bromoethynyl-1 -(2-trimethylsilylethoxymethyl)-4.6-dichlorindole-2-carboxylate Intermediate 4 was dissolved in dry THF (50 ml) and the solution was cooled to 0° in an ice/water bath. Lithium bis trimethylsilylamide (7.6 ml, 1.0 M sol. in THF) was slowly added from a syringe, the mixture stirred at 0° for 30 minutes and then quenched with saturated NH$_4$Cl (20 ml). Ethyl acetate was added, the two phases separated and the organic layer washed with 1N hydrochloric acid, dried and concentrated to dryness. The crude product was purified by column chromatography to give the title compound (2.9 g) as a yellow oil. Rf=0.35 CH/EA: 95/5

Intermediate 6

3-Bromoethynyl-1-(2-trimethylsilylethoxymethyl)-4.6-dichloroindole-2-carboxylic acid Intermediate 5 (2.9 g) was dissolved in ethanol 95% (40 ml), then LiOH.H$_2$O was added and the solution was stirred overnight at 80°. The reaction mixture was then concentrated to dryness and the resulting residue washed with 1 N HCl. After filtration the obtained solid was washed with water and dried over P$_2$O$_5$ to yield the title compound (2.6 g) as a white solid.

IR(Nujol)V$_{max}$(cm$^{-1}$) 1676(C=O), 1600(C=C). $^1$H—NMR(DMSO) 14.00(s), 7.90(d), 7.38(d), 5.92(s), 3.41(t), 0.76(t), −0.13(s).

Intermediate 7

Methyl 3-phenylcarbamoylethynyl-1-(2 -trimethylsilylethoxymethyl)-4,6-dichlorooindole-2-carboxylate Intermediate 6 (454 mg) was dissolved in dry THF (15 ml) and the solution cooled to −78°. A solution of t-butyl-lithium (1.3 ml, 1.7 M in hexane) was slowly added and the reaction mixture was stirred for 2 hrs. Phenylisocyanate (0.12 ml) was then, added and the mixture was gradually warmed to room temperature and stirred for 3 hrs. The reaction was quenched with saturated NH$_4$Cl and extracted with ethyl acetate. The combined organic phases were washed with 1N HCl, water and brine, dried and concentrated to dryness. The crude product was then, solubilized in dichloromethane (8 ml) and methanol (2 ml) and treated at room temperature with Me$_3$SiCHN$_2$ (1.2 ml, 1.0 M sol. in hexane). After 30 min of stirring, the solution was concentrate to dryness and the crude material was purified by flash chromatography (CH/EA:85/5) to give the title compound. (230 mg,) as a yellow solid.

Intermediate 8

(E)-Ethyl 3-[2-(phenylcarbamoyl)ethenyl]-1-(2-trimethylsilylethoxymethyl)-4,6-dichloroindole-2-carboxylate To a cooled (0°) solution of (E)-Ethyl-3-[2-(phenylcarbamoyl)ethenyl]-4,6-dichloroindole-2-carboxylate (300 mg) in dry DMF (25 ml) a solution of sodium bis-(trimethylsilyl)amide (1M;0.0814 ml) was added dropwise. The resulting mixture was stirred at room temperature for 30 minutes then cooled to 0°. Trimethylsilylethoxymethylchloride (185 mg) was added, and the reaction was stirred for one hour at room temperature. The resulting solution was poured in H$_2$O (20 ml) and extracted with diethylether (15 ml×3). The organic layers were dried, concentrated under vacuum and the product isolated by chromatography on silica gel(CH/EA:83/15) to give the title compound (311 mg). Rf =0.35 CH/EA:85/15

Intermediate 9

Ethyl 3-[(2-phenylcarbamoyl)-propenyl]-1-(2-trimethylsilylethoxymethyl)-4,6-dichloroindole-2-carboxylate P,P-Diethyl 2-phosphono-propananilide (644 mg) was dissovled in anhydrous DMF (10 ml) and the resulting solution cooled to 0° and treated with LiN(Me$_3$Si)$_2$ (2.3 ml of a 1.0M solution in THF) for 1.5 hour. Intermediate 3 (784 mg), separately dissolved in dry DMF (8 ml) was added to it and sitrring continued overnight. The reaction was quenched by pouring it into 50 ml of saturated NH$_4$Cl; the aqueous phase was then extracted with ethyl acetate and the organic layer washed with 1N hydrochloric acid, water and brine. dried, filtered and concentrated. Final purification by column chromatography yielded the title compound (660 mg) as an off-white solid. Rf=0.35, CH/EA 8.5/1.5

Intermediate 10

(E) Ethyl-3-[2-(phenylcarbamoyl)ethenyl]-4,6-dichloroindole-2- carboxylate

DBU (319 mg) was added to a stirred suspension of phenylcarbamoymethyl triphenylphosphoniumbromide (1 g) in acetonitrile (10ml) at under nitrogen. Stirring was continued at 0° for 15 minutes then intermediate 2 (680 mg) was added and the mixture refluxed for 6 hours. After dilution with dichloromethane (15 ml), the formed precipitate was collected by filtration giving the title compound (380 mg ;tlc EA/CH:3/7, Rf=0.5) as a white solid.

IR(Nujol) $V_{max}$(cm$^{-1}$)3305–3288(NH), 1678–1662(-C=O), 1627–1601(C=C). $^1$H-NMR (DMSO) 12.61 (s),10.20 (s), 8.27(d), 7.73(d), 7.52(d), 7.36–7.30(m), 7.06(m), 6.77(d), 4.39 (q), 1.36(t).

EXAMPLE 1

Methyl-3-[2-(phenylcarbamoyl) ethylnyl]-4.6-dichlorindole-2-carboxylate

Intermediate 7 was dissolved in ethanol 95% (18 ml) then HCl (18 ml; 5 N) was added dropwise and the solution was refluxed for 3 hrs. After addition of ethyl acetate (50 ml) the two phases were separated and the organic layer washed with water (2×40 ml), dried and purified by chromatography. The white solid (140 mg) obtained was dissolved in THF (4 ml), water (2 ml) and stirred at room temperature for 10 minutes. After cooling to 8°, LiOH-H$_2$O (42 mg) was added, the obtained mixture was stirred for 1 h. then poured into a solution of 0.01 N HCl and extracted with ethyl acetate. The combined organic layers were dried and concentrated under reduced pressure to give a residue which was titurated in ether affording the title compound (100 mrag) as a white solid. Rf=0.18 CE/EA: 70/30

IR(Nujol)$V_{max}$(cm$^{-1}$)3273(NH), 2220(C=C), 1686(C=C), 1636(C=O). 1H-NMR(DMSO) 13.5(s), 10.71(s), 7.68(m), 7.52(m), 7.40(d), 7.35(m), 7.11(m), 3.96(s).

EXAMPLE 2

3-[2-Phenylcarbamoyl)ethynyl]-4.6-dichloroindole2-carboxylic acid

A mixture of Example 1 (100 mg) tetrahydrofuran (4 ml), water (2 ml) and LiOH.H$_2$O (39 mg) was stirred at 45° for 12 hrs. Then, it was poured into water (15 ml) and HCl (0.05 M, 5 ml) was added dropwise under stirring. The obtained precipitate was collected by filtration to give the title compound as a yellow solid (63 mg,) m.p.=207°

IR(Nujol)$V_{max}$(cm$^{-1}$) 3169(NH-OH), 2240(C=C), 1745(C=O), 1661(C=O). 1H-NMR(DMSO) 13.05(s), 14.0(s), 12.88(s),10.7(s), 7.67(d), 7.51(d), 7.35(d),7.33(m), 7.10(m).

EXAMPLE 3

D.L.)-Trans-ethyl-3-[2-(2-phenylcarbamoyl)cyclopropyl]-4,6-dichloroindole-2-carboxylate (a)
(D.L.)-Trans-ethyl-3-[2-(2-phenylcarbamoyl)cyclopropyl]-1-(2-trimethylsilylethoxymethyl)-4.6-dichloroindole-2-carboxylate To a mixture of Intermediate 8 (0.1 g.) and Palladium-(II)acetate (4 mg) in dichloromethane (10 ml) under nitrogen at 0°, a solution of diazomethane in diethyl ether (8 ml, 0.125M) was added with stirring. A black solid was obtained with effervescence. The reaction was stirred for 15 hours at room temperature then the solvent and any remaining diazomethane were evaporated under a flow of nitrogen. Dichloromethane was added to the resulting residue which was filtered through celite and evaporated under reduced pressure. Purification by flash chromatography gave a mixture of starting material and title compound in ratio 0.3:1 (86 mg) as a pale yellow solid.

(b)
(D.L.)-Trans-ethyl-3-[2-(2-phenylcarbamoyl)cyclopropyl]-4.6-dichloroindole-2-carboxylate HCl (2 ml, 5M) was added to the product of Example 3a (66 mg) in ethyl alcohol (2 ml; 95%) and was stirred under reflux for 2 hours. After cooling, the mixture was poured into cold water (50 ml) and extracted with ethyl acetate (3×100 mol). The organic layers were combined, dried and the solvent was evaporated under reduced pressure to give the title compound (tic CH/EA=6/4; Rf=0.32).

IR (Nujol) $V_{max}$(cm$^{-1}$) 3312(NH), 1672(C=O), 1648 (C=O), 1599(C=C) 1535(C=C). $^1$H-NMR (CDCl$_3$) 12.1(s), 10.2(s), 7.60(d), 7.40(d), 7.28(t), 7.01(m), 4.40(m), 4.25(m), 2.55(m), 1.98(m), 1.49(m), 1.27(t), 1.22(m).

EXAMPLE 4

(D.L.)-Trans-3-[2-phenylcarbamoyl)cyclopropyl]-4.6-diichloroindole-2-carboxylic acid Starting from Example 3b (40 mg) and LiOH and using the general procedure of intermediate 11 the title compound was obtained as a white solid (23 mg). IR (Nujol) $V_{max}$(cm$^{-1}$) 3271(NH), 1663–1653(C=O), 1599 (C=C). $^1$H-NMR (DMSO) 13.4(s), 11.98(s), 10.11(s), 7.60(s), 7.37(d), 7.27(t), 7.17(d), 7.00(t), 1.97(m), 1.50(m), 1.47(m), 1.2(m).

EXAMPLE 5

Ethyl-3-[(2-phenylcarbamoyl)-propenyl]-4,6-dichloroindole-2-carboxylate

Intermediate 9 (660 mg) was dissolved in 95% EtOH (6 ml) and treated at reflux with 5N hydrochloric acid (6 ml) overnight. The solution was then taken up with ethyl acetate, washed with 1N hydrochloric acid, water and brine dried filtered and concentrated. Purification by column chromatgoraphy yielded the title compound (220 mg) as a white solid. Rf=0.30 CH/EA 7.5/2.5

$^1$H-NMR (DMSO) 12.48(s, 1H), 9.70(s,1H), 7.80–7.72(m,3H), 7.48(d,1H), 7.33(t,2H), 7.26(d,1H), 7.08(m,1H), 4.32(q,2H), 1.79(d,3H), 1.30(t,3H) ppm; IR (nujol) ($V_{max}$=cm$^{-1}$) 3317–3288 (str NH), 1678 (str CO).

EXAMPLE 6

3-[(2-Phenylcarbamoyl)-propenyl]-4,6-dichloroindole-2-carboxylic acid

Example 5(210 mg) was dissolved in 95% EtOH (6 ml) and treated with LiOH-H$_2$O (32 mg) at 30° for 1.5 days and then at room temperature for 2.5 days. The solution was then concentrated to dryness and treated for 2 hours with 1N hydrochloric acid. The white precipitate that formed was filtered, dried under high vacuum and then recrystallised from diethyl ethyl to give the title compound (135 mg) as a white solid.

$^1$H-NMR 13.5(s,1H), 12.37(s,1H), 9.70(s,1H), 7.76(d,2H), 7.75(s,1H), 7.45(d,1H), 7.31(t,2H), 7.23(d,1H), 7.06(t,1H), 1.78(d,3H)ppm. IR (nujol) ($V_{max}$—cm$^{-1}$) 3209(str, NH), 1664 (str, CO).

Pharmacy Examples

A. Capsules/Tablets

| Active ingredient | 200.0 mg |
|---|---|
| Starch 1500 | 32.5 mg |
| Microcrystalline Cellulose | 60.0 mg |
| Croscarmellose Sodium | 6.0 mg |
| Magnesium Stearate | 1.5 mg |

The active ingredient is blended with the other excipients. The blend can be used to fill gelatine capsules or compressed to form tablets using appropriate punches. The tablets can be coated using conventional techniques and coatings.

B. Tablet

| Active ingredient | 200.0 mg |
|---|---|
| Lactose | 100.0 mg |
| Microcrystalline Cellulose | 28.5 mg |
| Providone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with poviodone after dispersing in a suitable solvent (i.e. water). The granule, after drying and comminution is blended with the remaining excipients. The blend can be compressed using appropriate punches and the tablets coated using conventional techniques and coatings.

C. Injection Formulation

| Active ingredient | 0.1–7.00 mg/ml |
|---|---|
| Sodium phosphate | 1.0–50.00 mg/ml |
| NaOH qs desidered pH (range 3–10) | |
| water for injection qs to | 1 ml |

The formulation may be packed in glass (ampoules) with a rubber stopper (vials, syringes) and a plastic/metal overseal (vials only).

D. Dry Powder for constitution with a suitable vehicle

| Active ingredient: | 0.1–100.00 mg |
|---|---|
| Mannitol qs to | 0.02–5.00 mg | packed in glas vials or syringes, with a rubber stopper and (vials only) a plastic metal overseal.

E. Inhallation Cartridges

|  | mg/cartridge |
|---|---|
| Active ingredient (micronised) | 5.00 |
| Lactose to | 25.00 |

The active ingredient is micronised in a fluid energy mill to a fine particle size range prior to blending with normal tabletting grade lactose in a high energy mixer. The powder blend is filled into a proper unit does container as blister or capsule for use in a suitable inhalation or insufflation device.

The affinity of the compound of the invention for strychnine insensitvie glycine binding site was determined using the procedure of Kishimoto H. et al J. Neurochem 1981, 37,1015-1024. The pKi values obtained with respresentative compounds of the invention are given in the following table.

| Example No. | pKi |
|---|---|
| 2 | 7.7 |
| 6 | 8.32 |

The ability of compounds of the invention to inhibit NMDA included convulsions in the mouse was determined using the procedure of Chiamulera C. et al. Psychopharmacology 1990, 102, 551–552. In this test the ability of the compound to inhibit the generalized seizures induced by an intracerebroventricular injection of NMDA in mice was examined at a number of dose levels. From these results the dose required to protect 50% of the animals from the convulsive action of the NMDA was calculated,.This expressed as mg/kg is referred to as the $ED_{50}$ value. In this test the compound of Example 4 had an $ED_{50}$ value of 0.43 mg/kg when administered intravenously, and an $ED_{50}$ value of 3 mg/kg orally.

We claim:

1. A compound of formula (1)

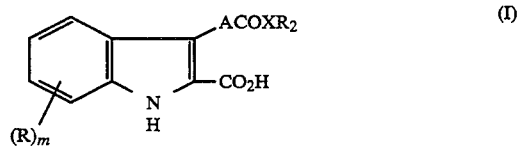

or a physiologically acceptable salt or metabolically labile ester thereof, wherein R represents a group selected from the group consisting of fluoro, chloro, boromo, $C_{1-4}$alkyl, $C_{1-4}$alkoxy, amino, $C_{1-4}$alkylamino, di-$C_{1-4}$alkylamino, hydroxy, trifuloromethyl, trifluoromethoxy, nitro, cyano, $SO_2R_1$ and $COR_1$, wherein $R_1$ represents hydroxy, methoxy or amino; m is zero or an integer 1or 2;

A represents an ethynyl group; an unsubstituted cyclopropyl group, a cyclopropyl group substituted by one, two or three $C_{1-4}$alkyl groups; an ethenyl group substituted by one or two $C_{1-4}$alkyl groups;

X represents —O— or NH;

$R_2$ represents phenyl; phenyl substituted with up to three substituents selected from the group consisting of fluoro, chloro, bromo, $C_{1-4}$alkyl, $C_{1-4}$alkoxy, amino, $C_{1-4}$alkylamino, di$C_{1-4}$alkylamino, trifluoromethyl, trifluorome4thoxy, hydroxy, cyano, nitro, amino, $SO_2R_1$ or $COR_1$ wherein $R_1$ is hydroxy, methoxy or amino; furanyl; thienyl; imidazolyl; thiazoyl; oxazolyl; pyridinyl or pyrimidinyl;

and when X represents an oxygen atom $R_2$ may also represent a hydrogen atom or a $C_{1-4}$ alkyl group.

2. A compound as claimed in claim 1 wherein m is 2 and R is chlorine at the 4 and 6 positions in the indole nucleus.

3. A compound as claimed in claim 1 wherein $R_2$ is a substituted phenyl group.

4. A compound as claimed in claim 1 wherein $R_2$ is phenyl.

5. A compound as claimed in claim 1 wherein X is NH.

6. A compound as claimed in claim 1 wherein A is ethynyl, or substituted ethenyl.

7. A compound as claimed in claim 1 wherein A is ethynyl or 1-methylethenyl in the trans configuration.

8. (E)-3-[2-phenylcarbamoylpropenyl]-4,6-dichloroindole-2-carboxylic acid; and physiologically acceptable salts and metabolically labile esters thereof.

9. (E)-3-[2(Phenylcarbamoyl)ethynyl)-4,6-dichloroindole-2-carboxylic acid; and physiologically acceptable salts and metabolically labile esters thereof.

10. A compound as claimed in claim 1 wherein the metabolically labile ester is a $C_{1-4}$-alkyl ester, an amino $C_{1-4}$alkyl ester or an acyloxy $C_{1-4}$alkyl ester.

11. A compound as claimed in claim 8 wherein the metabolically labile ester is a $C_{1-4}$alkyl ester, an amino $C_{1-4}$alkyl ester or an acyloxy $C_{1-4}$alkyl ester.

12. A compound as claimed in claim 9 wherein the metabolically labile ester is a $C_{1-4}$alkyl ester, an amino $C_{1-4}$alkyl ester or an acyloxy $C_{1-4}$alkyl ester.

13. A pharmaceutical composition comprising a compound in claim 1 in admixture with one or more physiologically acceptable carriers or excipients.

14. A method of treatment of a mammal including man for conditions where antagonishing the effects of excitatory amino acids on the NMDA receptor complex is of therapeutic benefit comprising administration of an effective amount of a compound as claimed in claim 1.

* * * * *